United States Patent
Plunkett et al.

(10) Patent No.: US 7,282,105 B1
(45) Date of Patent: Oct. 16, 2007

(54) SUPPORT PLANAR AND TAPERED QUASI-PLANAR GERMANIUM WAVEGUIDES FOR INFRARED EVANESCENT-WAVE SENSING

(76) Inventors: Susan E. Plunkett, 2319 New Berne Rd., Richmond, VA (US) 23228-6019; James J. Stone, 104 Fourth St. NE. #2, Charlottesville, VA (US) 22902; Mark Stephen Braiman, 131 Butler St., Syracuse, NY (US) 13210

( * ) Notice: Subject to any disclaimer, the term of this patent is extended or adjusted under 35 U.S.C. 154(b) by 879 days.

(21) Appl. No.: 10/320,895

(22) Filed: Dec. 17, 2002

Related U.S. Application Data

(63) Continuation-in-part of application No. 09/426,055, filed on Oct. 25, 1999, now Pat. No. 6,496,636, which is a continuation-in-part of application No. 08/874,711, filed on Jun. 13, 1997, now Pat. No. 5,980,831.

(60) Provisional application No. 60/106,132, filed on Oct. 29, 1998.

(51) Int. Cl.
B32B 31/00 (2006.01)
G02B 6/10 (2006.01)
(52) U.S. Cl. ............... 156/154; 385/129; 385/123; 156/153
(58) Field of Classification Search ........... 385/129, 385/123; 156/153, 154
See application file for complete search history.

(56) References Cited

U.S. PATENT DOCUMENTS 3,831,115 A * 8/1974 Coldren ............... 333/150

5,980,831 A 11/1999 Braiman et al.
6,496,636 B1 12/2002 Braiman et al.

OTHER PUBLICATIONS

Plunkett, s. et al, "Supported Planar Germanium Waveguides for infrared Evanscent-Wave Sensing", Applied Optics, vol. 36, No. 18, Jun. 20, 1997, pp. 4055-4061.*

* cited by examiner

*Primary Examiner*—Jeff H. Aftergut
(74) *Attorney, Agent, or Firm*—Jagtiani + Guttag

(57) ABSTRACT

Miniature planar IR waveguides of thickness 30–50 μm, consisting of 12-mm long, 2-mm wide strips of Ge supported on ZnS substrates and tapered quasi-tapered waveguides, tapered from a thickness of 1 mm at the ends to a minimum of 1–100 μm at the center, are disclosed. The surface sensitivity is increased as a function of incidence or bevel angle. The tapered waveguide improves the efficiency of the optical coupling both into the waveguide from an FTIR spectrometer, and out of the waveguide onto a small-area IR detector. The tapering makes it possible to dispense with using an IR microscope couple light through the waveguide, enabling efficient coupling with a detector directly coupled to an immersion lens. This optical arrangement makes such thin supported waveguides more useful as sensors, because they can be made quite long (e.g. 50 mm) and mounted horizontally. Furthermore, even with a 20-μm× 1-mm cross section, sufficient throughput is obtained to give signal/noise ratios in excess of 1000 over most of the 1000–5000 cm$^{-1}$ range, with just 2 min of scanning at 8 cm$^{-1}$ resolution.

12 Claims, 12 Drawing Sheets

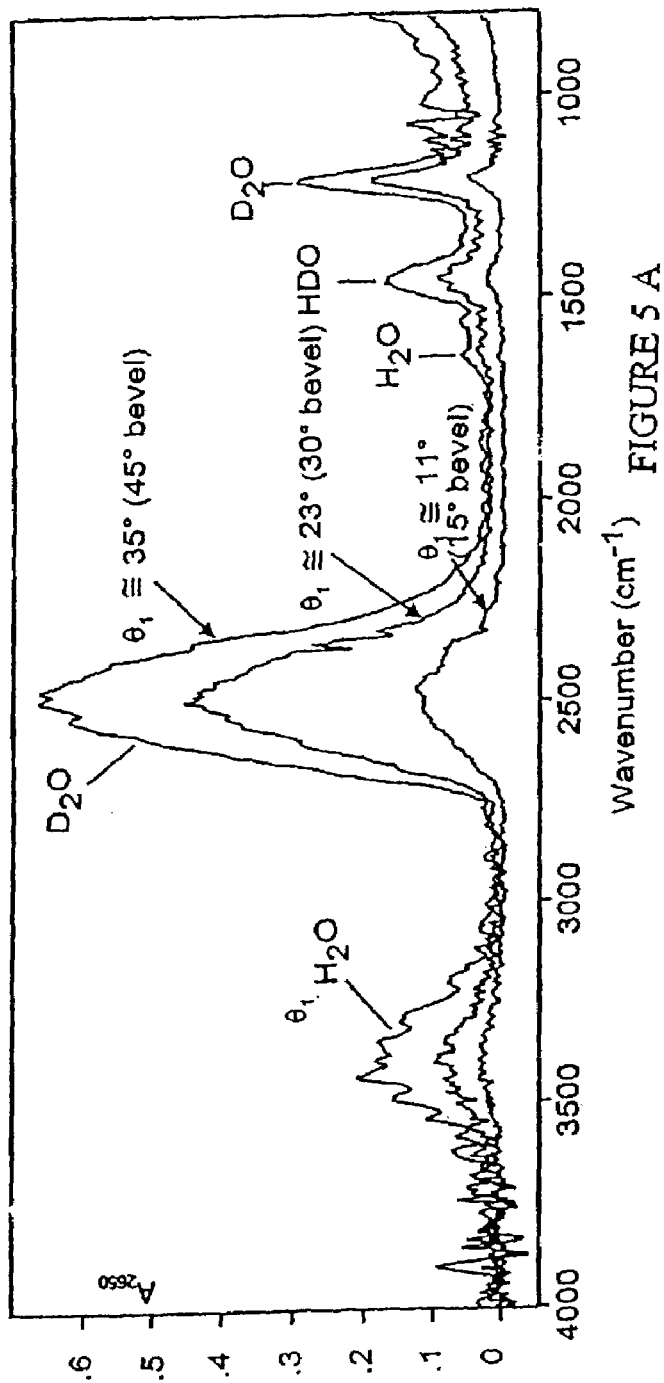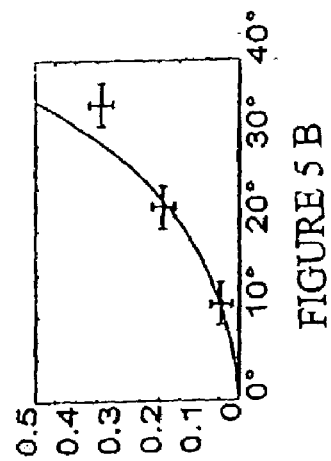
FIGURE 5 A
FIGURE 5 B

SUPPORT PLANAR AND TAPERED QUASI-PLANAR GERMANIUM WAVEGUIDES FOR INFRARED EVANESCENT-WAVE SENSING

CROSS-REFERENCE TO RELATED APPLICATIONS

This application is a continuation-in-part of Ser. No. 09/426,055, now U.S. Pat. No. 6,496,636, filed Oct. 25, 1999 and issued on Dec. 17, 2002 which is a continuation-in-part of Ser. No. 08/874,711, now U.S. Pat. No. 5,980,831, filed Jun. 13, 1997 and issued Jun. 13, 1997. The present application further claims the benefits under 35 U.S.C. 119(e) of copending provisional patent application Ser. No. 60/106,132, filed Oct. 29, 1998. This application incorporates by reference, as though recited in full, the disclosure of parent U.S. Pat. Nos. 6,496,636 and 5,980,831 and copending provisional patent application Ser. No. 60/106,132.

GOVERNMENT GRANTS

This work was supported by NSF grants MCB-9722887 and MCB-9406681 to Mark S. Braiman.

BACKGROUND OF THE INVENTION

The development of mid-infrared (IR) waveguides has been driven by their use as remote or small-sample-size chemical sensors for surface sensitive spectroscopy. Such waveguides can be thought of as miniaturized multiple reflection elements (MREs) wherein the incident light undergoes total internal reflection at the interface between media of different refractive indices. At each internal reflection within the waveguide, a portion of the optical field, the evanescent wave, extends beyond the high-index waveguide into the adjacent low-index medium, to a depth ($d_p$) dependent on the angle of incidence and the ratio of the two refractive indices. The ability of molecules outside the high-index waveguide, but near its surface, to absorb energy travelling through the waveguide via this evanescent wave makes possible the phenomenon known as attenuated total reflection (ATR) or evanescent-wave spectroscopy (EWS).

In the IR region, high-refractive-index materials as Ge, Si, and KRS-5 ($Tl_2BrI$), cut and polished as prisms having trapezoidal or parallelogram cross-sections and dimensions on the order of 50×20×2 mm, are in common use for EWS measurements. These macroscopic waveguides typically have throughputs matched to commercial FTIR spectrometers, i.e. in the vicinity of 1–10 $mm^2$-stearadian. Commercially available IR fiber optics (multimode cylindrical waveguides made of, e.g., chalcogenide glass), have more recently been used as EWS sensors. These optical fibers typically have much lower throughputs than the prism MREs, complicating somewhat their use with commercial IR spectrometers. Nevertheless, when properly coupled to a small-area (low-noise) IR detector, fiber optics display the advantage that miniaturization enables smaller amounts (μL) of sample to be detected. This advantage arises from the fact that, while the surface sensing area is smaller, the light experiences a larger number of reflection per unit length of waveguide, yielding a concomitant increase in evanescent path length. It would be desirable to see how far this advantage could be extended, i.e. how thin an EWS waveguide or fiber could be made. However, it becomes impractical to make a free-standing IR fiber less than ~50 μm in diameter.

Most thin planar waveguide development has been in the visible region, where low-loss transparent materials (polymers and glasses) are commercially available and easy to manipulate. Such waveguides have generally been used in conjunction with single-frequency lasers, which provide high luminosity, monochromaticity, and fine control over the launch angle, and have been used for absorption, Raman, and fluorescence analytical methods. In contrast, IR-transmissive materials with the requisite high refractive indices and low attenuation values are either very brittle, or have not had techniques developed to allow them to be deposited (e.g. by evaporation or sputtering techniques) as uniform and well-adhered films of the desired thicknesses of 1–100 μm.

BRIEF SUMMARY OF THE INVENTION

The disclosed supported planar and tapered, quasi-planar waveguides provide increased broadband transmission and demonstrate many of the characteristics predicted by planar waveguide theory. In particular, they show a great increase in the sampling sensitivity as compared to previous evanescent-wave absorption measurements.

There are three particularly novel aspects to the fabrication and use of the disclosed thin supported planar IR waveguides. First, the waveguides have been generated by physically "whittling away" at a macroscopic piece of highly transparent single-crystal materials, such as Ge., rather than by attempting either to deposit or to modify chemically a thin film of transmissive material. The latter are the most common approaches for generating thin-film waveguides. For example, sputtering is the only method to have been used previously in an attempt to fabricate thin-film Ge light guides for wavelengths in the 2–10 μm range. However, this attempt results in a waveguide with rather high attenuation of about 20 dB per cm, due to scattering from the non-uniformly-deposited Ge. It is possible to detect transmission of $CO_2$ laser light through such a waveguide, however attempts at detecting broadband transmission through similarly-fabricated thin-film-sputtered waveguides, e.g. 1-μm thick Ge on $CaF_2$, have failed. This is likely due to the much lower luminosity of the broadband light source available, as compared to the $CO_2$ laser used in prior art testings. The disclosed devices enable success in obtaining IR transmission using the weaker broadband source through the development of waveguides with much lower scattering losses than currently are obtainable with sputtered Ge films.

The disclosed waveguides further have an added "cladding" for the waveguide's supported surface, in the form of a rather thick vacuum-deposited layer of a cladding material such as ZnS. This turns out to be crucial for fabrication and use, since it is difficult to attach the piece of bulk single-crystal Ge to a substrate without using IR-absorbing adhesive materials. Only by protecting the Ge with the vacuum-deposited cladding is it possible to use simple cements or optical adhesives to attach it firmly enough to allow grinding and polishing to a few-μm thickness.

The disclosed waveguide further uses a direct method to couple light into and out of its ends. Such direct coupling is generally not used for monochromatic (e.g. laser) light; more efficient coupling methods exist (e.g. prism coupling) that depend on optical interference effects. However, use of curved mirrors with foci at the two ends of a waveguide is probably the most generally useful means of coupling a broad bandwidth of light into it. This has long been known to be true for macroscopic MREs used for EWS. This is also be true for waveguides of arbitrarily thin dimension, although in some thickness ranges, the waveguides show considerable oscillations of throughput, as disclosed below.

Supported planar IR Ge waveguides, having a thickness between 50–100 μm, are useful as mid-IR evanescent-wave sensors. A significant portion of the light energy transmitted through such waveguides actually propagates outside the germanium, as an evanescent wave in the surrounding medium. With <100-μm-thick waveguides, a very small number of IR— absorbing molecules near the surface of the waveguide can significantly attenuate the light transmitted through the waveguide, allowing the measurement of an ATR (attenuated total reflection) spectrum. Sizable ATR bands are therefore observed from thin surface layers under 1 mm² in area. This includes thin coatings on small pieces of polymer film, as well as patches of the plasma membrane of large individual cells, e.g. frog oocytes.

One difficulty with using thin planar Ge waveguides as internal reflection elements (IREs) is coupling measurable amounts of light through such waveguides and onto a detector. Prior art requires the use of an IR microscope in order to measure useful spectra through waveguides having a thickness between 30–100 μm. Use of a microscope, however, results in significant limitations on the waveguide configurations that can be used. In particular, waveguide lengths were generally limited to ~12 mm, the maximum separation between objective and condenser focal points on commercial FTIR microscopes. Furthermore, the waveguides had to be positioned vertically, i.e. along the optical axis of the microscope. This is an inconvenience for samples containing liquids, especially small biological samples.

A quasi-planar waveguide, preferable made from single-crystal germanium, is also disclosed wherein one of the surfaces has an arcuate contour while a parallel, second surface is planar, the first surface being concave relative to the second surface. The perimeter is comprised of multiple opposing planar surfaces at right angles to the second surface. The second surface is coated with a cladding, such as ZnS and then adhered to a substrate, such as quartz. The substrate must have a perimeter at least equal to that of the waveguide and a thickness sufficient to support the waveguide. The arcuate surface of the waveguide has an apex at least about four times greater than the nadir, with a preferred ratio of nadir to apex taper of at least about 1:10 and up to about 1:50. For clarity and consistency, the ratio can also be reviewed from the reverse standpoint, that is, apex to nadir. Thus, the ratio of apex to nadir is up to 0.25:1. The preferred ratio of nadir to apex is in the range from about 0.01:1 to about 0.25:1. The nadir of the waveguide is less than 100 μm, and preferably in the range of 1 to 20 μm. The arcuate surface is polished to about a 0.1 μm finish to prevent light scattering. The tapered waveguide can also be coupled directly to an IR detector, eliminating the need for a microscope and enabling more accurate alignment. The elimination of the microscope also enables the waveguide to be mounted horizontally. The tapered waveguide increases IR signal throughput by about 4–5 fold, a result of filling the large numerical aperture of a high-index waveguide medium (Ge, n=4). This increase, for a given sensor thickness, makes it possible to detect the IR signal level more precisely in a shorter length of time. With an untapered planar waveguide, the largest numerical aperture that can be attained inside the waveguide is equal to the numerical aperture of the element that focuses light through air onto the end of the waveguide. This must always be less than 1, and for commercially available focusing optics is typically 0.5–0.8. On the other hand, the fundamental limitation on the largest numerical aperture that can be propagated inside a dielectric waveguide is the refractive index of the waveguide material and it's cladding, and is equal to $(n_1^2-n_2^2)^{1/2}$. Here n1 is the refractive index of the waveguide medium ($n_1$=4 for Ge), while $n_2$ is the highest refractive index of the cladding materials in contact with the waveguide ($n_2$=2.26 for ZnS). For the disclosed ZnS-clad Ge waveguide, this maximum numerical aperture is 3.3, or approximately 4-fold higher than the numerical aperture of available focusing optics. In theory, at least ~4-fold more light energy can be propagated through the sensing region of a planar Ge waveguide than can be obtained by focusing light through air into the edge of an untapered waveguide of the same minimum thickness. This theoretical maximum throughput is, in fact, closely approached with the tapered waveguide design.

BRIEF DESCRIPTION OF THE DRAWINGS

FIG. 5A graphs the FT-IR evanescent-wave absorbance spectra of a 1-μL $D_2O$ droplet on the waveguide for each of the three bevel angles ($\theta_2$=15°, 30°, and 45°);

FIG. 5B graphs the absorbance at 2650 $cm^{-1}$;

DETAILED DESCRIPTION OF THE INVENTION

The waveguides manufactured herein are from germanium prisms, however as the advantages over prior art waveguides are obtained through the science rather than the materials, other elements can be substituted. For example, silicon or cadmium tellurium, will behave similarly, although the mechanical properties of these, and other, materials will require attention to procedures. For example, CdTe is significantly more brittle than Ge and therefore requires additional care during the grinding procedures. When selecting a cladding layer or substrate, the physical properties in relation to one another and to the waveguide material must be taken into account. For example, when selecting a cladding material, the strength of attachment to the waveguide and to the cement/substrate must be considered. Selection of a substrate must take into consideration the rigidity, optical transparency in the UV and the ability to reach a high degree of flatness in surface polish. The Ge/ZnS/quartz combination disclosed herein provides an example of the desirable material interaction and can be used as a baseline for comparison.

Additional disclosure is contained in applicants' publication entitled, "Design for Supported Planar Waveguides for Obtaining Mid-IR Evanescent-Wave Absorption Spectra from Biomembranes of Individual Cells", Mark S. Braiman, and Sysan E. Plunkett, Volume 51, Number 4, April 1997, Applied Spectroscopy, copyright 1997, Society for Applied Spectroscopy, the disclosure of which is incorporated herein, by reference thereto, as though recited in full.

Another additional disclosure is contained in applicants' publication, entitled, "Mid-IR evanescent-wave absorption spectra of thin films and coatings measured with a ~50-micrometer planar Ge waveguide sensors", James J. Stone, Mark S. Braiman, and Susan E. Plunkett, published Jun. 15, 1997, Process SPIE, the disclosure of which is incorporated herein, by reference thereto, as though recited in full.

Fabrication of Thin Supported Planar Waveguides.

Infrared waveguides were fabricated from commercially available prisms of Ge and ZnS. The Ge prisms were purchased as 12×2×2-mm orthorhombs from Spectral Systems, and were each coated on one 12×2-mm side with a 2-µm-thick layer of ZnS using chemical vapor deposition (CVD). The ZnS-coated side of each Ge prism was then cemented with polycyanoacrylate adhesive to a ZnS substrate (25×12×2-mm orthorhomb). As shown by repeated failed attempts to transmit light through uncoated waveguides, the IR-transparent layer between the Ge waveguide and the adhesive is absolutely necessary to prevent the IR light from being completely attenuated by the strongly absorbing polycyanoacrylate.

Figure 1:
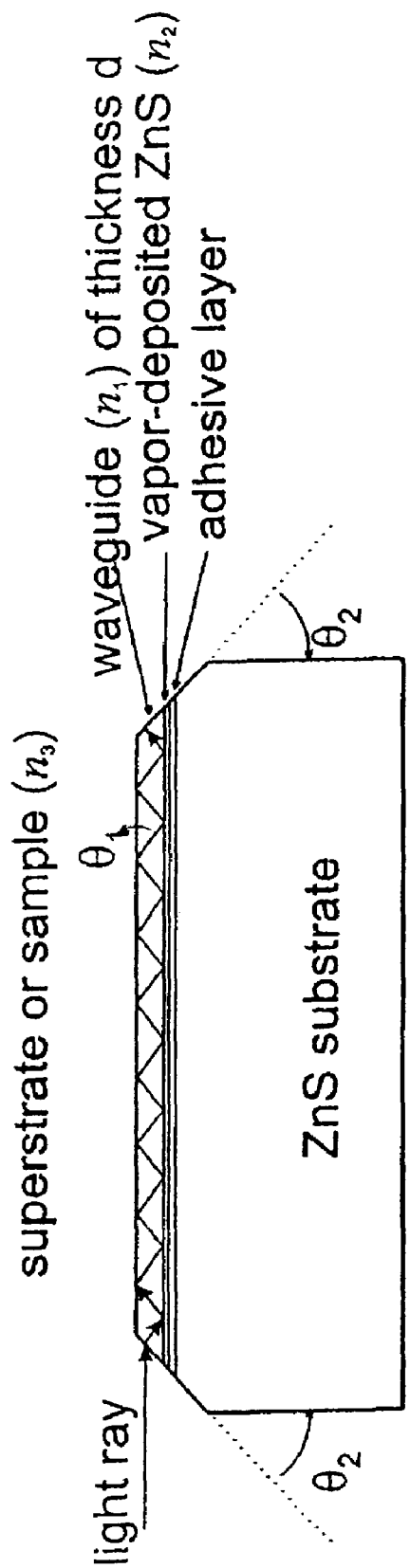
FIG. 1 is a schematic of the supported planar Ge waveguide used for infrared evanescent-wave sensing.
Figure 2:
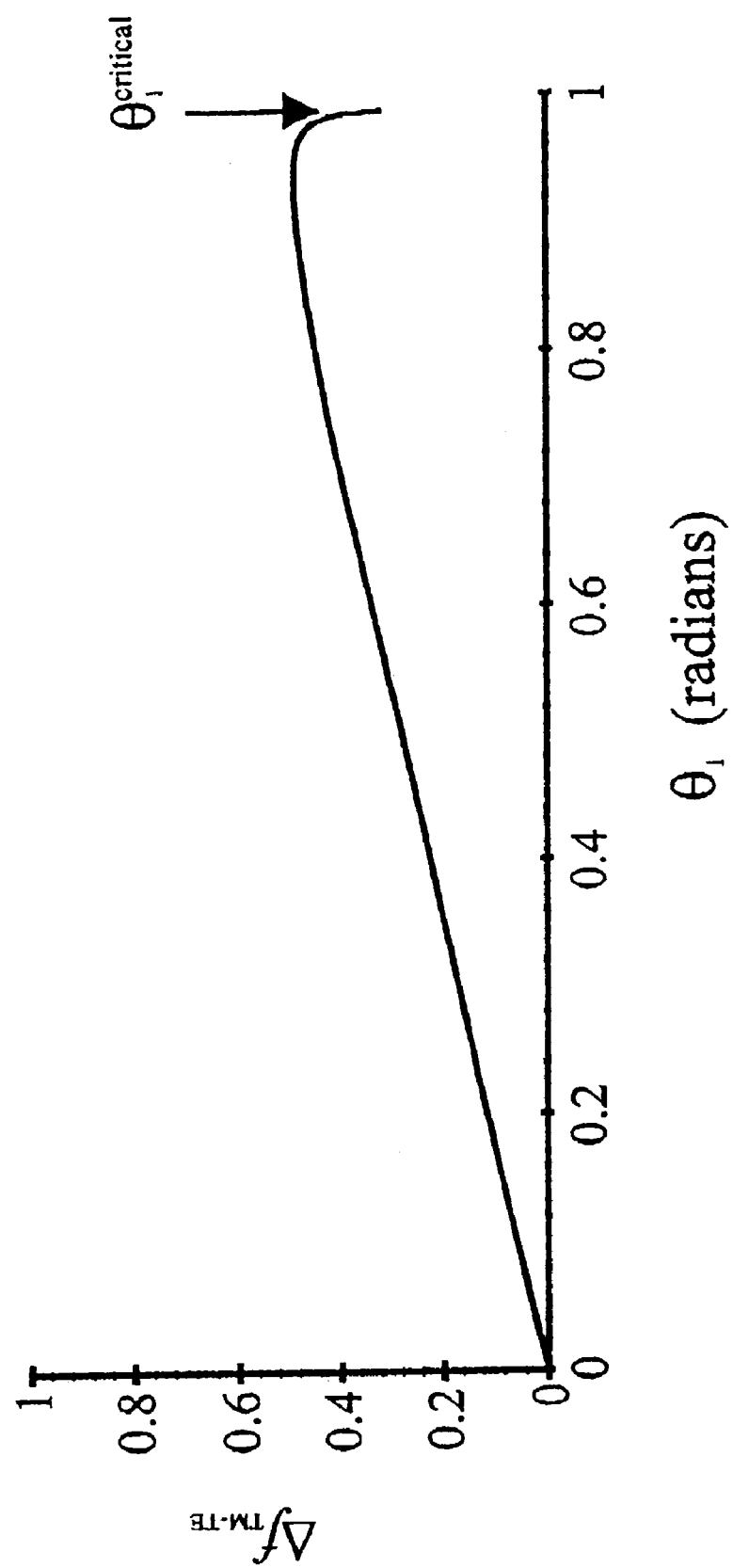
FIG. 2 illustrates the separation $\Delta f_{TM-TE}$ between the oscillatory transmission patterns for TE and TM modes, normalized to the common mode spacing shared by both, and plotted as a function of $\theta_1$, the internal propagation angle measured relative to the waveguide surface plane.

The 2 mm-thick supported Ge strip was then ground and polished by hand to a final thickness of 30–100 µm using the abrasive powders and flat glass polishing stone in a commercially available polishing kit (Harrick, Ossining, N.Y.). For the final steps of polishing, the abrasive powders were replaced by $Al_2O_3$ lapping paper. The final thickness and degree of polish of each waveguide were measured with a visible light microscope. Typically the observed random surface scratches were less than 3 µm in depth. Beveled ends were ground on the waveguide (and the substrate below) using PTFE guides cut to the desired angle, using the same lapping paper. A schematic of a typical waveguide is shown in FIG. 1 where $\theta_1$ is the internal propagation angle; $\theta_2$ is the launch or bevel angle; and $n_1$, $n_2$, $n_3$ are the refractive indices of the waveguide, substrate, and superstrate, respectively.

Broadband infrared light was focused through the waveguide and measured using an IR microscope (IR-Plan™ Infrared Microscope Accessory, Spectra-Tech, Stamford, Conn.), interfaced to an FT-IR spectrometer. This IR microscope was selected because it is one of the only models available that permits the separate focusing of the objective and condenser mirrors on the input and output ends of the waveguide, some 12 mm apart. Light exiting the waveguide was collected and focused onto a photoconductive HgDcTe dectector having $(0.1 \text{ mm})^2$ active area (Graseby Infrared, Model FTIR-M 16-0.10). Data processing was done with GRAMS 386 software (Galactic Industries, Salem, N.H.).

Oscillations in the single-beam throughput spectrum of a planar waveguide arise from the requirement to satisfy one of the two eigenvalue equation one of the two eigenvalue equations of a planar waveguide in order to obtain transmission. For a defined thickness and propagation angle, each of these two equations (see below), which correspond to the two possible polarizations, is satisfied only at a set of evenly-spaced light frequencies. The spacing is the same for both polarizations, and is thus observed even when observing the transmission with unpolarized light.

This was achieved by starting from a standard theory of planar dielectric waveguides, and deriving expressions that relate the period of the oscillations ($\Delta\bar{v}$) in the broadband IR transmission spectrum to three experimentally fixed parameters of the waveguide: thickness d, refractive index ($n_1$), and propagation angle $\theta_1$ or bevel angle $\theta_2$ (defined by the diagram in FIG. 1). The planar waveguide sensors are considered as approximations to the well-studied asymmetric planar slab waveguide, where waveguide, substrate, and superstrate have refractive indices $n_1$, $n_2$, $n_3$, respectively. Using the shorthand notations $n_{21}=n_2/n_1$ and $n_{31}=n_3/n_1$, then the eigenvalue equations are:

$$\tan \kappa d = \frac{\kappa(\gamma + \delta)}{\kappa^2 - \gamma\delta} \text{(for guided } TE \text{ modes)}$$

$$= \frac{\kappa(n_{21}^2\gamma + n_{31}^2\delta)}{n_{21}^2 n_{31}^2 \kappa^2 - \gamma\delta} \text{(for guided } TM \text{ modes)}$$

The parameters $\kappa$, $\gamma$, and $\delta$ are characteristic of the mathematical solutions to Maxwell's equations in the waveguide, the substrate, and the superstrate, respectively. For waveguides that are thick compared to the wavelength of light propagating inside them, these variables can be approximated as simple functions of a well-defined propagation angle $\theta_1$. To enable the defined propagation angle, only a spectral region of sufficiently short wavelength (<10 µm in vacuo, or <2.5 µm inside the Ge), compared to the waveguide thickness d (30–50 µm) was considered. We will therefore make the substitutions $\kappa=2\pi n_1\bar{v}\sin\theta_1$; $\gamma=2\pi\bar{v}(n_1^2\cos^2\theta_1-n_2^2)^{1/2}$; $\delta=2\pi\bar{v}(n_1^2\cos^2\theta_1-n_3^2)^{1/2}$. These are equations 1.3-26, 1.3-63, and 1.2-13 through 1.2-15, 1, with minor mathematical rearrangements, as found in Theory of Dielectic Optical Waveguides, Marcuse, D., Academic Press, N.Y., 1991.

Hereinafter it is disclosed that, because of the very high refractive index of Ge ($n_1$=4.0), the propagation angle $\theta_1$ is almost equal to the bevel angle $\theta_2$ of the ends of the waveguide, regardless of what range of angles of light are focused on the input end and collected from the output end of the waveguide. Therefore a value of $\theta_1$ is used, calculated by assuming simple Snell's-law behavior for a central (axis) ray of the microscope's light-focusing mirror system, i.e. $\theta_1 = \theta_2 - \arcsin[\sin(\theta_2/n_1)] \cong 0.75\theta_2$.

The eigenvalue equations can now be re-cast in terms of the experimental parameters $\bar{v}=1/\lambda$ (the wavenumber of the light); the propagation angle $\theta_1$; and the refractive indices $n_1$, $n_2$, and $n_3$. From the resulting simplified eigenvalue equation, the allowed solutions of $\bar{v}$ at externally fixed values of $\theta_1$ and d can be obtained. Note that this differs from the more common approach of examining the solutions of $\theta_1$ at fixed values of $\bar{v}$ and d.

The right sides of equations 1 and 2 are both independent of light frequency $\bar{v}$, since every factor of this parameter in the numerator is balanced in the denominator. Thus, the two eigenvalue equations reduce to $$\tan \kappa d \epsilon \{E_{TE}, E_{TM}\}$$

where $$E_{TE} = \frac{\sin\theta_1[(\cos^2\theta_1 - n_{21}^2)^{1/2} + (\cos^2\theta_1 - n_{31}^2)^{1/2}]}{\sin^2\theta_1 - (\cos^2\theta_1 - n_{21}^2)^{1/2}(\cos^2\theta_1 - n_{31}^2)^{1/2}} \text{ and }$$

$$E_{TM} = \frac{\sin\theta_1[n_{21}^2(\cos^2\theta_1 - n_{21}^2)^{1/2} + n_{31}^2(\cos^2\theta_1 - n_{31}^2)^{1/2}]}{n_{21}^2 n_{31}^2 \sin^2\theta_1 - (\cos^2\theta_1 - n_{21}^2)^{1/2}(\cos^2\theta_1 - n_{31}^2)^{1/2}}$$

are simply two constants determined by the parameters $\theta_1$, $n_1$, $n_2$, and $n_3$ for a particular waveguide geometry. The set of solutions to the simplified form of the eigenvalue equation is now easily obtained:

$$\kappa d = \arctan E + \pi N; E \in \{E_{TE}, E_{TM}\}$$

$$\bar{v} = \frac{f + N}{2 n_1 d \sin\theta_1}; f \in \left\{\frac{\arctan E_{TE}}{\pi}, \frac{\arctan E_{TM}}{\pi}\right\}$$

Figure 3:
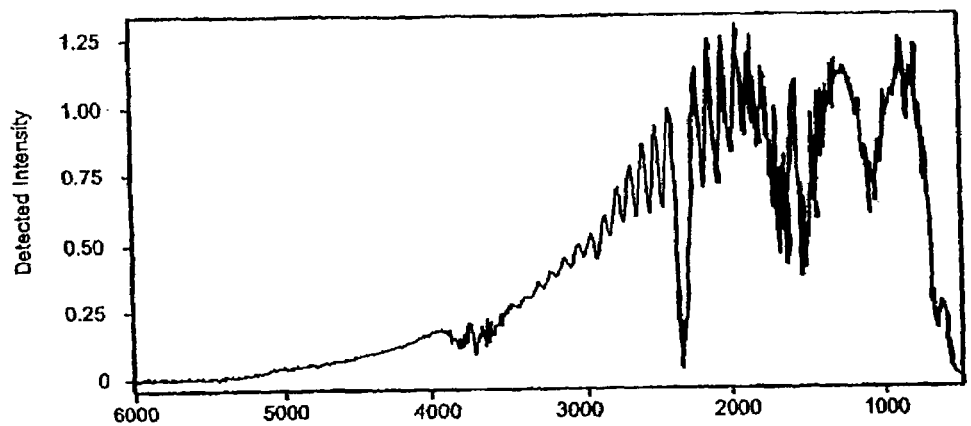
FIG. 3A graphs the uncorrected FT-IR single-beam intensity throughput spectrum for a typical 50-μm-thick waveguide with 15° bevel angles FIG. 3B graphs the intensity spectrum, corresponding to FIG. 3A, of a rectangular aperture set to the same size as the cross-section as the waveguide (2 mm×50 μm)
FIG. 3C graphs the Ge spectral high and low frequency cutoffs.
Figure 3:
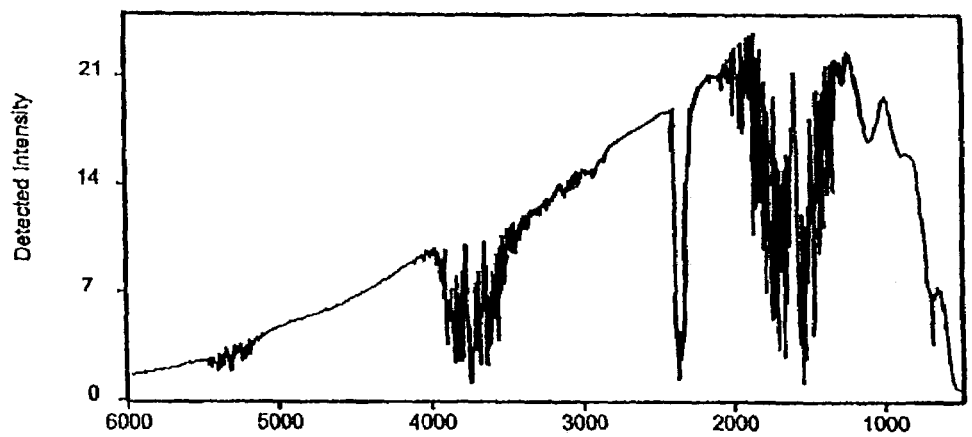
Figure 3:
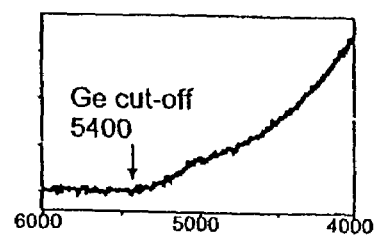

In both of the preceding equations, N is allowed to take on any integer value. That is, the allowed TE and TM frequencies are each expected to be evenly spaced, with a period of $\Delta\bar{v}=1/(2n_1 d \sin \theta_1)$. The calculated separation between the TE and TM series, $\Delta f_{TM-TE}$=(arc tan $E_{TE}$–arc tan $E_{TM}$)/$\pi$, is expected to be 0 for $\theta_1$=0, and to increase roughly linearly with $\theta_1$, until very close to the critical angle. For the materials used by us ($n_1$=4.0, $n_2$=2.2, $n_3$=1), $\Delta f_{TM-TE}$ is plotted as a function of $\theta_1$ (in radians) in FIG. 3.

Depending on the separation between TE and TM modes, it is easier or more difficult to see their shared oscillation period in the throughput spectrum obtained with unpolarized light. At low values of $\theta_1$, where the TE and TM modes are expected to be separated by much less than a single oscillation period, they should superimpose quite well, making it easy to see an interference pattern. At values approaching the critical angle, however, the TE and TM modes are expected to be almost perfectly interleaved, leading to an apparent period that is only half of the actual period $1/(2n_1 d \sin \theta_1)$ and to a smaller-amplitude intensity oscillation that is much harder to observe on the gradually-changing throughput spectrum. This actually turns out to be quite desirable for a broadband evanescent-wave sensor.

FIG. 3A shows the uncorrected FT-IR single-beam intensity throughput spectrum for a typical 50-μm-thick waveguide with 15° bevel angles. It is compared with the open-beam throughput spectrum of the microscope through a rectangular aperture the same size as the cross-section of the waveguide (2 mm×50 μm) shown in FIG. 3B. The sharply-delineated spectral features present in both waveguide and open-beam spectra near 1650, 2200, and 3800 are absorption bands due to gaseous water and carbon dioxide. These are present since the beam path in the IR microscope contained room air, (i.e., was unpurged). FIG. 3C illustrates an expansion of the 6000–4000 cm$^{-1}$ region, clearly showing the high frequency transmission cutoff of Ge at ~5400 cm$^{-1}$. The most obvious novel feature in the waveguide throughput spectrum is the rapidly-oscillating beat pattern, superimposed on the normal throughput, in the 2000–3500 cm$^{-1}$ region. As discussed further below, this interference pattern corresponds closely to the mode structure predicted by waveguide theory, and is the clearest demonstration that light is being guided though the thin layer of Ge. Additionally, the waveguide shows characteristic Ge spectral high and low frequency cut-offs at 5400 cm$^{-1}$ (see inset) and 550 cm$^{-1}$.

It should also be noted that even below 5400 cm$^{-1}$, the spectral intensity transmitted through the waveguide decreases with increasing frequency much faster (relative to the maximum value near 2000 cm$^{-1}$) than in the open-beam spectrum. This drop-off is an indication of the scattering losses due to imperfections on the waveguide surface(s). The less thoroughly the surface of the waveguide was polished, the more drastic was the drop-off. It would almost certainly be possible to improve on the high frequency throughput, since commercial polishers routinely obtain better finishes on optics than obtained by hand polishing. The overall measured transmittance of the waveguide at 2000 cm$^{-1}$ is about 5% relative to an aperture of the same cross-section. The reflection losses from the two air-Ge interfaces at the ends of the waveguide are about ~50%, based on measurements of the transmittance through a Ge window. Thus the waveguide has an attenuation of about 10 dB over its entire 12-mm length. This means that the disclosed 50-μm thick Ge waveguide has about 10-fold less attenuation than a 1-cm-long, 5-μm thick Ge waveguide sputtered onto a KRS-5 substrate, for which the attenuation was estimated as 20 dB per cm, and through which light transmission was detected only by using a powerful $CO_2$ laser.

Figure 4:
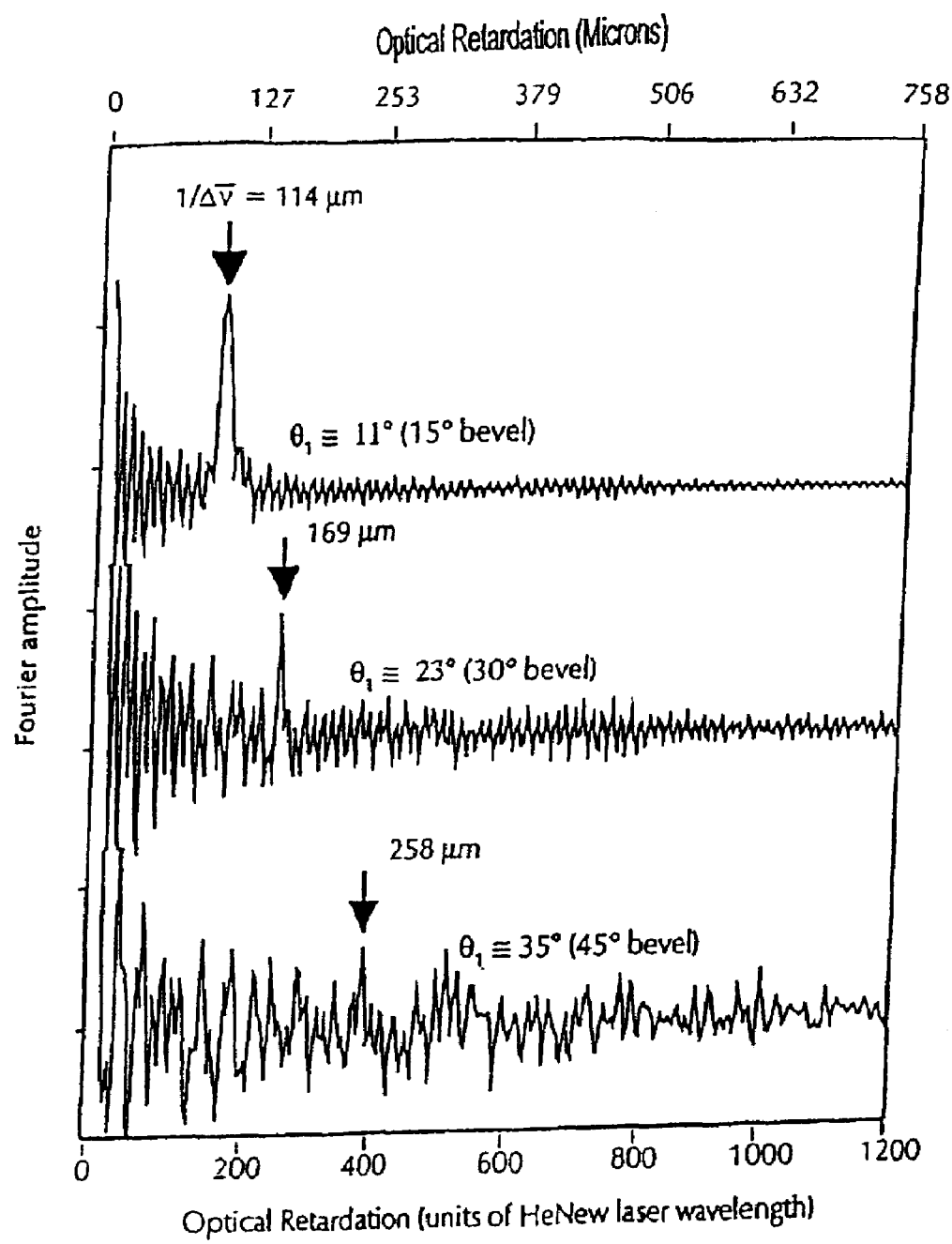
FIG. 4A Fourier transforms of the single-beam intensity throughput of the 50-μm-thick waveguide with $\theta_2$=15°, 30°, and 45° bevels.
FIG. 4B graphs the TE-polarized light of FIG. 4A.
Figure 4:
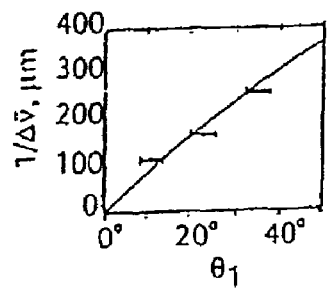
Figure 6:
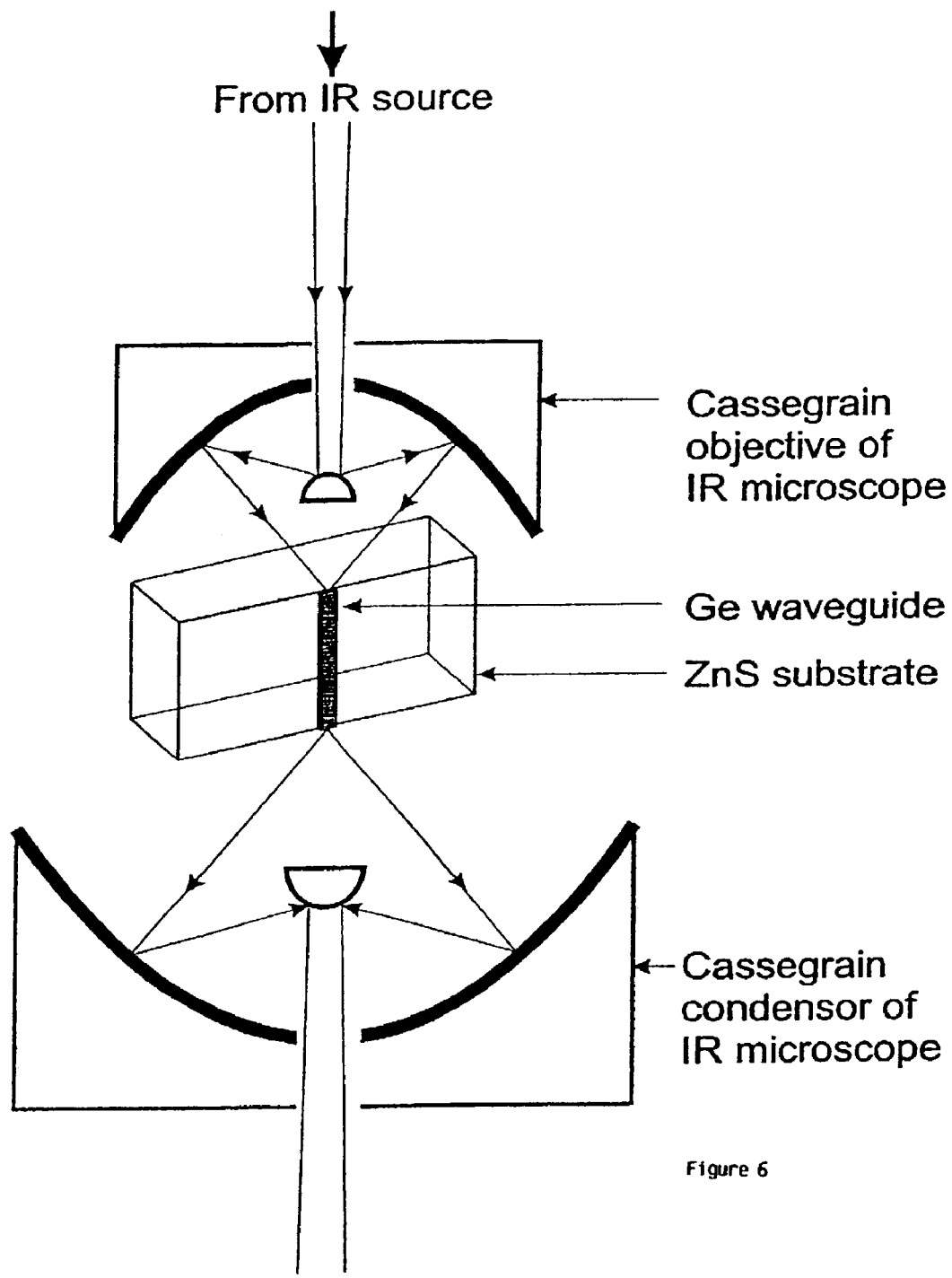
FIG. 6 is a schematic representation illustrating an IR light path from the source of the IR light, through the objective of an IR microscope, through a germanium waveguide, and showing the light collected by the condenser mirror and focused onto a detector.

FIG. 4A shows Fourier transforms of the 4400–2430 cm$^{-1}$ region of the throughput spectra for bevel angles ($\theta_2$) of 15°, 30°, and 45°. In each, the spike feature associated with the oscillatory (beat) pattern in the spectrum is indicated with an arrow. Each spectrum, measured as in FIG. 4A, was truncated at 4400 and 2430 cm$^{-1}$, then apodized using a Blackman-Harris 3-term function, and Fourier transformed. The phase was corrected to obtain just the amplitude of the Fourier transform. The 15° and 30° data were obtained with unpolarized light. However, as $\theta_1$ increases, the amplitude of the oscillatory pattern in the spectrum decreases, because the TE- and TM-mode beat patterns move "out of phase" and cancel each others' intensity. Therefore, data at 45° were obtained using TE-polarized light (using a wire grid polarizer). With unpolarized light at 45°, the spike in the corresponding plot is just barely visible, at nearly the same point as obtained with the TE-polarized light. FIG. 4B plots the reciprocal of the oscillation period ($1/\Delta\bar{v}$) versus internal propagation angle ($\theta_1$). The filled circles are experimental data and the straight line is the theoretically predicted behavior: $1/\Delta\bar{v}=(2n_1 d \sin \theta_1)$ with $n_1$=4.0, d=50 μm, and $\theta_1=\theta_2$–arc sin[sin($\theta_2/n_1$)]. The main source of error in this plot was imprecision in grinding the bevel angle $\theta_2$. The error bars in the inset show the resulting ±5° uncertainty in $\theta_1$.

These plots provide the most precise measurement of the period of the oscillating beat pattern, since a sine wave in the spectrum corresponds to a spike in its Fourier transform. The optical retardation at this spike is just the reciprocal of the oscillation period $\Delta\bar{v}$ in the spectrum. The inset is a plot of the reciprocal of the oscillation period ($1/\Delta\bar{v}$) versus internal propagation angle ($\theta_1$). The filled circles are experimental data and the straight line is the theoretically predicted behavior using Equation (3) above for unpolarized light: $1/\Delta\bar{v}=(2n_1 d \sin\theta_1)$ with $n_1$=4.0, d=50 μm, and $\theta_1=\theta_2$–arc sin [sin($\theta_2/n_1$)]. It is apparent that there is a close correlation between experimental and theoretical values.

FIG. 5A shows absorbance spectra for a ~2 mm-diameter $D_2O$ droplet on the waveguide for each of the three bevel angles. $D_2O$ (deuterated water) was chosen since it adheres well to the waveguide, evaporates slowly, and exhibits well-known absorption bands in spectral regions unobscured by absorption due to $H_2O$ vapor. Bands at ~2500 cm$^{-1}$ and 1250 cm$^{-1}$ are due to D-O stretch and DOD bend vibrations, respectively. The smaller bands at 3400 cm$^{-1}$ and 1450 cm$^{-1}$ are due to H-O stretch and H-O-D bend vibrations, and resulted from rapid H/D exchange of the droplet with $H_2O$ in the room air over the course of the 30-minute measurement. The degree of exchange was similar for all 3 measurements, as was the decrease in droplet size (20% –30% over 30 min) due to evaporation. FIG. 5B plots the absorbance at 2650 cm$^{-1}$ versus internal propagation angle $\theta_1$. The filled circles are experimental data and the straight line is the theoretically predicted behavior for TE-modes (see text). The $A_{2650}$ values were each increased to take into account the absorbance at ~3500 cm$^{-1}$ resulting from H/D exchange. The horizontal error bars represent our estimate of ±5° uncertainty in the bevel angle; the vertical error bars result from noise in the spectrum and uncertainty in the degree of H/D exchange. As the bevel angle increases, surface sensitivity (detected IR absorbance per unit sample contact area) also increases. This phenomenon is the result of three well-established relationships of the bevel angle ($\theta_1$) to detected intensity: (1) the evanescent field penetration depth ($d_p$) increases with $\theta_1$ up to $\theta_{critical}$; (2) the interfacial evanescent field intensity increases monotonically with $\theta_1$, up to 90°; and (3) the number of internal reflections increases monotonically with $\theta_1$. At low angles $\theta_1$, the measured absorbance is expected to be roughly a quadratic function of sin $\theta_1$. The measured IR absorbance A is related to known parameters of the water ($D_2O$) sample and waveguide jby multiplying the right side of Harrick's equation 2–25, which describes the coupling of the evanescent wave to an absorbing medium at a single internal reflection, by the number of internal reflections at which the $D_2O$ droplet is sensed. This number is tan $\theta_1 \times l/2d$ (remembering that the absorbing medium is present on only one side of the waveguide). For simplicity, we assume the use of TE-polarized light. Corresponding expressions for TM-polarized or unpolarized light are somewhat more complicated but of a similar magnitude, and exhibit a roughly similar dependence on $\theta_1$.

$$A = \frac{k_3 n_{31}^2 l}{(1-n_{31}^2)d} \frac{\sin^2\theta_1}{\cos\theta_1 (\cos^2\theta_1 - n_{31}^2)^{1/2}}$$

Here $k_3$ is the imaginary refractive index of the sample (estimated for $D_2O$ at ~150 cm$^{-1}$ above its 2500-cm$^{-1}$ absorption maximum, by using a published value of 0.13 for $H_2O$ at a corresponding frequency displacement from its 3350-cm$^{-1}$ absorbance maximum); $n_{31}$ is the ratio of the (real) refractive index of the sample to that of the waveguide, 0.33; l is the contact length of the $D_2O$ droplet with the waveguide surface (2.5 mm); d is the waveguide thickness (50 μm); and $\theta_1$ is the internal angle of propagation, which we varied.

The inset to FIG. 5 is a plot of IR absorbance at 2650 cm$^{-1}$ ($A_{2650}$) versus internal propagation angle ($\theta_1$). The filled circles are experimental data and the straight line is the theoretically predicted behavior. For this plot, a wavenumber somewhat away from the absorbance maximum was selected, to reduce problems due to absorbance flattening. This is a well-known phenomenon in EWS that arises due to the inaccurate assumption of only a single internal propagation angle $\theta_1$, and only a single contact length l for the roughly-circular water droplet. In fact, the use of focusing optics with large numerical aperture means that for each bevel angle $\theta_2$, light traversing the waveguide has a range of internal propagation angles $\theta_1$. Furthermore, the interaction length l is significantly shorter for light traversing the waveguide near the edges of the 3-mm-diameter droplet than for light near the center. Both of these factors mean that there is actually a range of effective path lengths through the sample in each of the measurements. This results in a sublinear dependence of absorbance on average effective path length, i.e. a non-Beer's Law type of behavior, as we actually observe. The deviation of measured data from theoretical dependence on θ was even greater when a wavenumber closer to the absorbance maximum of 2500 cm$^{-1}$ was selected (not shown).

The large surface sensitivity demonstrated in FIG. 5 is a significant improvement over previous studies using optical fibers for evanescent-wave IR spectroscopy. For instance, Simhony et al, achieved an absorbance of only 0.5 for the most intense band in the $H_2O$ spectrum (3350 cm$^{-1}$); using an immersion length of 65.5-mm for a 900-μm diameter silver halide ($AgCl_xBr_{1-x}$) fiber optic in water. The same absorbance value (0.5) was obtained for a 70-mm length of 500-μm diameter chalcogenide fiber, using a different coupling method that resulted in a different set of propagation angles $\theta_1$ than in the silver halide fiber experiment cited. The vast increase in sensitivity in the current study is due to the thinness (d) of the waveguide, as well as the ability to polish its supported ends at a bevel angle ($\theta_2$) of up to 45°. As mentioned above, the number of internal reflections per unit length varies as tan $\theta_2$/d. Therefore, a 10-fold reduction in thickness (500 μm to 50 μm), and an increase of $\theta_2$ from 10–15° maximum for a free-standing fiber to 45–50° for our supported waveguide, has yielded over a 30-fold decrease in the sample contact length required to obtain an absorbance reading of 0.5.

Tapered Quasi-Planar Waveguides

The thin, mid-IR-transmitting, waveguide sensors disclosed overcome the prior art difficulties in light coupling light through use of a gradual bi-directional taper. Tapering has been used for some years as a means of improving the optical throughput of small cylindrical waveguide sensors, e.g. glass optical fibers. Cylindrical fiber tapered wave guides can be produced by melting/softening and drawing, an approach that is not directly applicable to planar Ge waveguides. To produce a tapered thin planar waveguide is technically more difficult than tapering a cylindrical chalcogenide fiber, especially when the goal is to achieve a sensor thickness below 100 μm.

The melting/softening and drawing combination has been used for years to produce tapered shapes for waveguides as well as glass micropipettes, etc. The drawing process, when applied to a softened region of a piece of glass of arbitrary shape, tends to produce a taper that is more and more cylindrically symmetrical the longer the drawing is carried out. There is no comparably simple process for generating a quasi-planar waveguide shape from a softened piece of glassy material.

The simplest procedure would be to roll a softened piece of glassy material against a hard surface. A tapered thickness is produced by this process, but with nowhere near the surface polish that is attainable for a drawn glass taper of cylindrical symmetry. An additional problem is that the resulting "waveguide" has irregular edges, which cause problems in the throughput. Ideally, a flat nearly planar waveguide should have linear, or perhaps smoothly curved, edges. Thus, it would appear that cylindrical fiber tapered waveguide concepts are not applicable to non-cylindrical, non-fiber waveguides.

The disclosed tapered, "quasi-planar," waveguides have properties that make them particularly useful for certain types of mid-IR evanescent-wave sensors. The term "quasi-planar" as employed herein, refers to a waveguide that has a single planar surface, and a secondary "quasi-planar" parallel surface. The quasi-planar surface deviates from a true planar surface in that it is an arcuate. This tapering improves the efficiency of the optical coupling both into the waveguide from an FTIR spectrometer, and out of the waveguide onto a small-area IR detector. The tapering further enables the elimination of an IR microscope to couple light through the waveguide. Instead, it is possible to obtain extremely efficient coupling with a detector directly coupled to an immersion lens. This optical arrangement enables the disclosed tapered waveguides to be useful as sensors, because it simplifies the positioning of optical accessories needed to couple light into the waveguide. Untapered waveguides require a microscope or other bulky focusing mirrors close to the waveguide, thereby blocking easy access to its surface for depositing materials to be analyzed. Additionally, the elimination of the IR microscope permits the sensors to be mounted horizontally, an added advantage when using liquids. Furthermore, using a Ge waveguide having a 20- µm×1-mm cross section, sufficient throughput is obtained to give signal/noise ratios in excess of 1,000 over most of the 1000–5000 $cm^{-1}$ range, with two (2) minutes of scanning at 8 $cm^{-1}$ resolution. The small (0.02 $mm^2$) cross section of the waveguide yields great sensitivity to small numbers of IR-absorbing molecules near its surface. The optimum thickness for the waveguide is 1-µm, however due to the output obtained with the 20-µm waveguides, in many applications the increased output obtainable by 1-µm will not provide any advantages.

Figure 7:
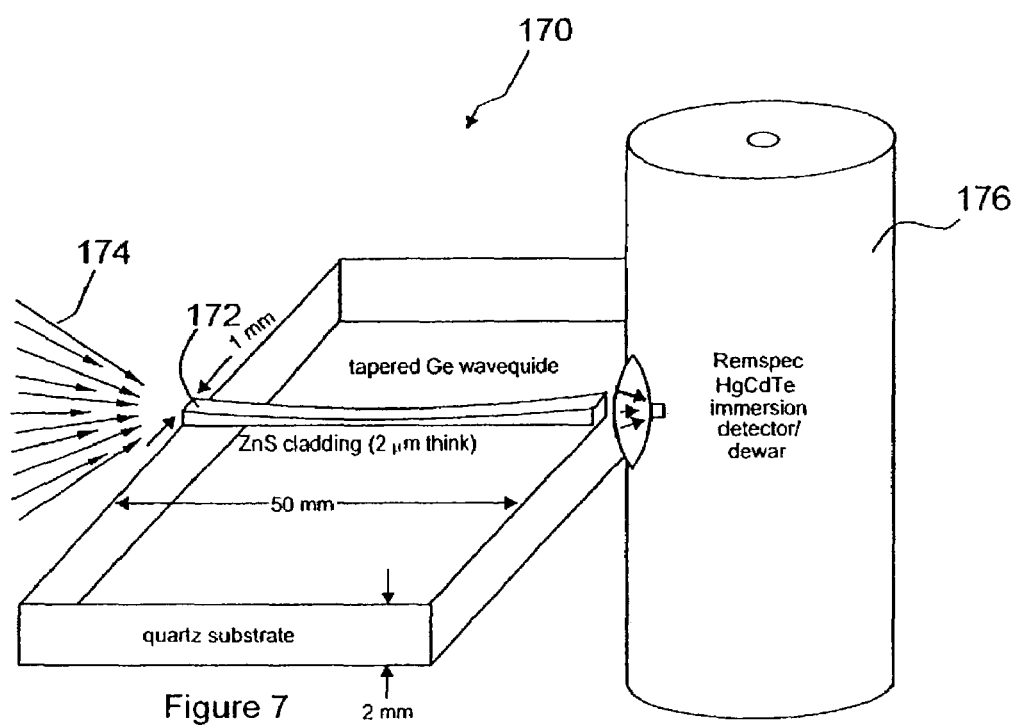
FIG. 7 is a schematic diagram of a tapered quasi-planar Ge waveguide and it's coupling to an IR detector.

As illustrated in the schematic diagram 170 of FIG. 7, the disclosed quasi-planar Ge waveguide 172 has been coupled to an IR detector 176, such as sold by Remspec Instruments, model MOD-02. The focused input light 174, shown at left of the figure, is typically from an FTIR spectrometer. In this embodiment, one of the flat surfaces of the waveguide 172 is first coated with a thin cladding layer of ZnS, or an equivalent coating, then cemented to a rigid substrate 178, such as quartz. The top, unadhered, surface of the waveguide 172 is ground to a large-radius arcuate shape having a cylindrical sector of radius ~300 mm. Preferably a commercial tool for grinding concave cylindrical lenses is used to grind and polish the waveguide, to enable the accurate tapering of the prism.

Although the end thickness, or apex, is not necessarily critical, the apex should be at least 4-fold thicker than the minimum thickness, or nadir, at the middle. The ends should also have a thickness no greater than the width of the waveguide for optimum optical performance using commercially available IR detector elements, which are square or circular. To obtain optimum performance, the waveguide end should be imaged onto the detector without any overhangs.

Fabrication Of Tapered Quasi-Planar Waveguides

Tapered Ge waveguides are fabricated using modifications of previously published procedures, using a commercial tool for grinding the concave cylindrical lenses. Greater care is needed to avoid scratching the waveguide surface as it is more difficult to fix any scratch or gouge once it has occurred. This greater care includes in the selection and maintenance of grinding/polishing surfaces.

To make the tapered waveguides shown in FIG. 7, custom polished 50×20×1 mm Ge prisms are used as the starting material. They are coated on one face with a 1.2-µm-thick CVD coating of ZnS and then cemented to 50×50×2-mm quartz substrates using a UV-curing optical adhesive. The substrate dimensions must be at least that of the prism to provide support, however, the dimensions beyond the periphery of the prism are determined by end use and convenience in handling. To form the tapered surface, the waveguides are ground using aluminum oxide grinding powders against a commercially available cylindrical grinding tool with an appropriate diameter. The coarser techniques are used until the tapered portion has almost reached the desired thickness. Pads, designed for use with curved surfaces, are used with the grinding tool and the powders to create the grinding/polishing surface. The thickness of the middle can be determined by observing the interference pattern between reflections from the front and back surfaces of the Ge waveguide in an FTIR spectrum with an IR microscope in reflectance mode. At that point, the curved surface is polished with a slurry combination of aluminum oxide (12.5 µm) and diamond powder (0.1 µm) and particle embedded soft films. Careful fine polishing to a 0.1- µm, or below, finish is crucial for minimizing light scattering from imperfections in the surface. To accomplish the required finish, the films are covered with water during the polishing process with the particle size within the embedded films decreasing with each polishing, i.e. 12.5, 9, 6, 3, 1, 0.5, 0.3 and 0.1-µm.

In the event the Ge prisms are not available at the desired end thickness, the prisms can be ground against a flat glass, or equivalent grinding stone, to the final thickness. The curved surface is then ground and polished as set forth above.

Figure 8:
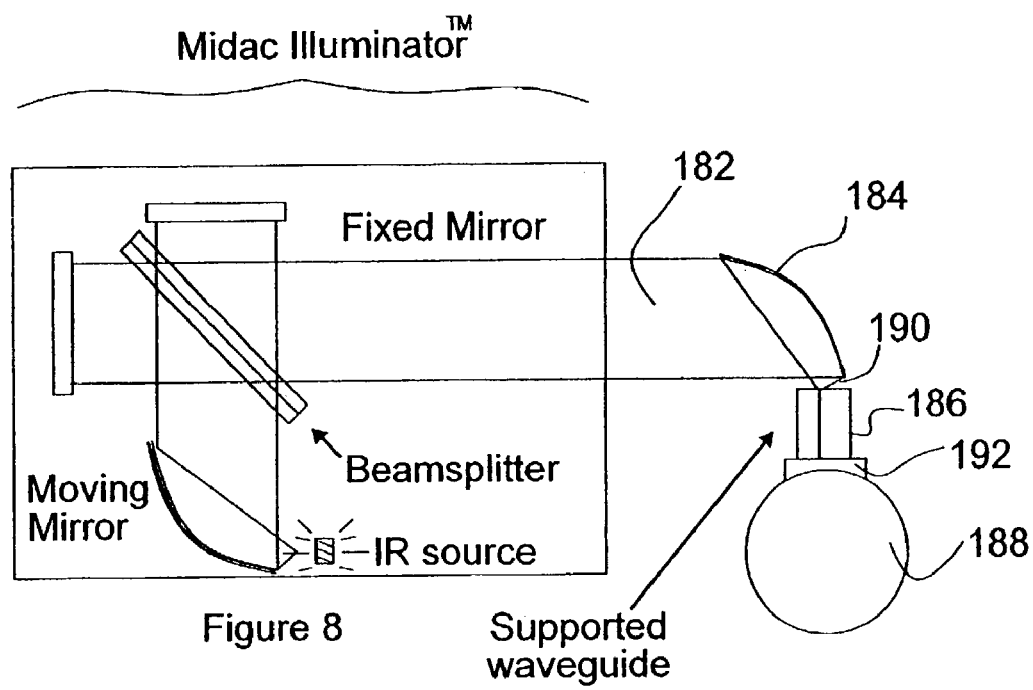
FIG. 8 is schematic of an optical arrangement used to observe broadband IR transmission or attenuation spectra through tapered quasi-planar Ge waveguide.

In FIG. 8 collimated light output by a commercial FTIR spectrometer 182 with a blackbody source is focused along a horizontal optical axis, into the 1-$mm^2$ entrance aperture 190 of the vertically placed waveguide 186, by using a single off-axis paraboloid mirror 184 (f=25 mm). Alignment at the output end 192 of the waveguide 186 is greatly simplified by using a Remspec immersion detector 188, which has a short focal length IR-transmitting lens 194 directly in contact with the small-area HgCdTe detector 196. The output end 192 of the tapered waveguide 186 is placed as close as possible to the lens 194 and along its axis.

Figure 9:
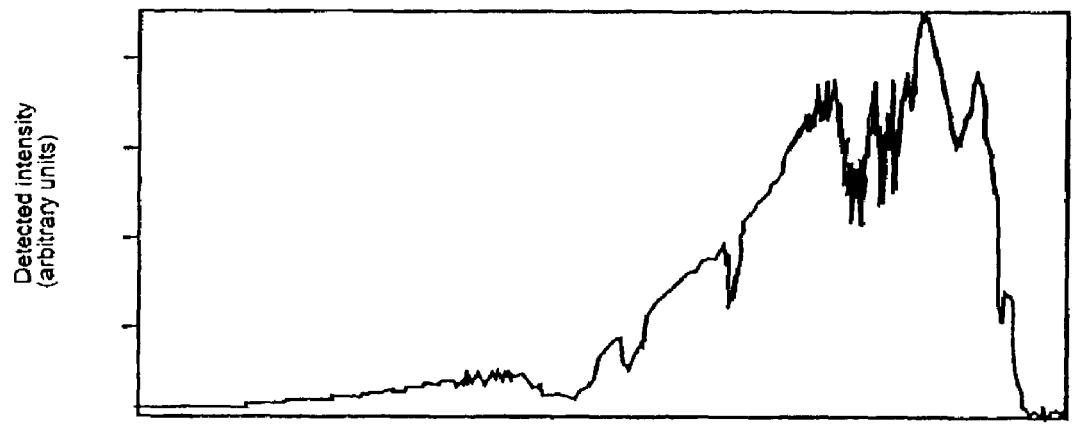
FIG. 9A is a graph illustrating the transmission properties of the disclosed 20-μm-thick tapered waveguide.
FIG. 9B is a graph illustrating a transmittance noise spectrum using the disclosed tapered waveguide.
FIG. 9C is a graph illustrating the cutoff of transmission at 5100$cm^{-1}$ using a prior art planar waveguide.
Figure 9:
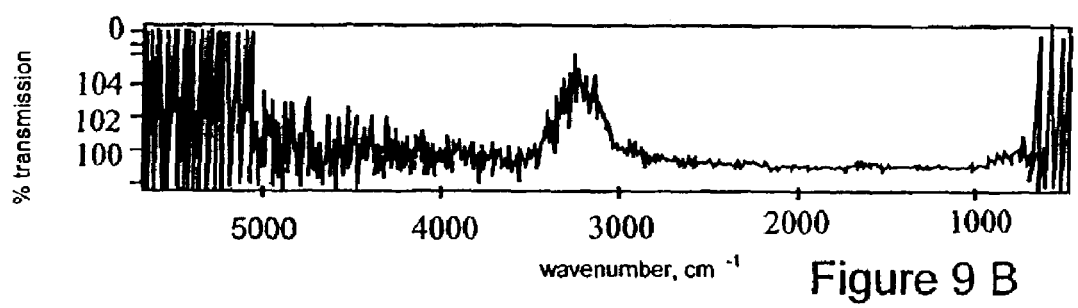
Figure 9:
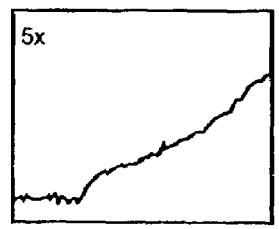

As illustrated in the graphs of the optical arrangement shown in FIGS. 9 and 10, broadband optical throughputs sufficient to saturate the Remspec detector/preamp combination 188 are easily achieved through a planar Ge waveguide of 20-μm thickness. Spectral measurements through this waveguide, measured with 8-cm-1 resolution over a bandwidth of 0–7900 cm$^{-1}$, have a signal/noise ratio in excess of 1000 after only 2 min scan time (see FIG. 9). This signal/noise ratio applies over the range 1000–2500 cm$^{-1}$.

However, there are some notable differences in the signal/noise ratio at sub-regions within the spectral range of 1000–2500 cm$^{-1}$. The relatively larger depletion of light at higher frequencies is due to greater scattering losses from imperfections at the surfaces of the thinner waveguide. Since all surface phenomena are magnified with a thinner waveguide, it is crucial to polish the tapered waveguide surface as thoroughly as possible.

The light spectrum transmitted through the 20-μm thick tapered waveguide, and graphed in FIG. 9, is similar in most respects to that transmitted through flat Ge planar waveguides. The disclosed waveguide, however, increases the total amount of light transmitted through the waveguide, per unit cross-sectional area at the waveguide's thinnest point, by 4–5 fold greater than a planar waveguide.

The intensity spectrum from FTIR spectrometer with broadband blackbody IR source, shown in 9A, uses an HgCdTe detector, and reflects data gathered from the arrangement of FIGS. 7 and 8. In particular, the distinct cutoff of transmission near 5100 cm$^{-1}$, as illustrated in by the inset of FIG. 9C, is characteristic of light transmitted through a prior-art planar Ge waveguide. The sharp attenuation bands near 2300 and 2000–1400 cm$^{-1}$ are due to atmospheric $CO_2$ and $H_2O$ vapor, respectively, in the open path of the IR beam. In 9B, 100% transmittance noise spectrum calculated from the ratio of two successive single-beam intensity spectra, each acquired in 2 min (1000 scans) with 8-cm$^{-1}$ resolution is graphed. The tapered waveguide has a broad intrinsic absorption band near 3500 cm$^{-1}$ that leads to substantial baseline irregularities in ratioed spectra (FIG. 9B). The peak-to-peak transmittance noise in the 2000–2200 cm$^{-1}$ range is 0.1%. The peak-to-peak transmittance noise from the tapered waveguide is less than 0.2 as large as that measured in the same amount of time using a planar waveguide with a similar thickness.

The transmission spectrum of the tapered waveguide is especially unique for a feature that it lacks, namely the oscillatory interference pattern characteristic of planar waveguides with a fixed thickness and propagation angle. The observed oscillations in transmitted intensity arise from a fixed frequency separation between allowed waveguide modes. With the tapered waveguide, there is a wide range of propagation angles as well as a wide range of waveguide thicknesses. This results in a superposition of oscillation patterns continuously covering a wide range of different periods, i.e. no discernible oscillatory pattern at all.

Figure 10B:
FIG. 10B is a graph illustrated the attenuated total reflection (ATR) spectra of a solid film sample obtained with the disclosed tapered 20-μm-thick waveguide.
Figure 10A:
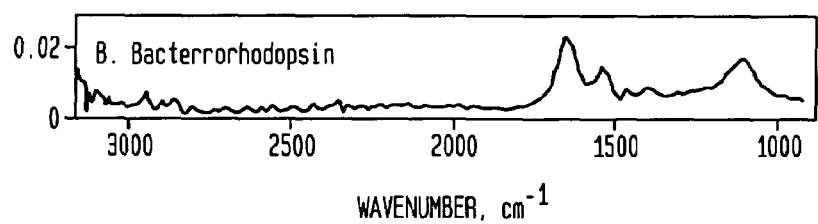
FIG. 10A is a graph illustrating the attenuated total reflection (ATR) spectra of a liquid sample obtained with the disclosed tapered 20-μm-thick waveguide.

FIG. 10A shows the attenuated total reflection (ATR) spectra of a liquid while FIG. 10B shows the ATR of a solid film sample. Both were obtained with a tapered 20-μm-thick waveguide and the light source and detector illustrated in FIGS. 7 and 8. The two samples shown are deuterated water ($D_2O$) and a thin film of halobacterial membrane containing lipid (25%) and protein (75%). In each case, the spectrum presented is $-\log(I/I_o)$, where I is the intensity spectrum measured in the presence of sample, and Io is the spectrum measured in its absence. In each case the sample covered a region ~1 mm in area at the thinnest central region of the waveguide, the measurement time was 2 min (500 scans), and spectral resolution was 8 cm$^{-1}$.

The $D_2O$ sample was measured with a 1-μL droplet covering only a ~1-mm length of the thinnest portion of the waveguide. Coverage of longer regions of the waveguide produced only small increases in the size of the absorbance bands. (Data not shown). The graph of FIG. 10A shows a strong O-D stretch vibration near 2500 cm$^{-1}$ and weaker D-O-D bending vibration near 1250 cm$^{-1}$.

The dried film of ~2 pmol bacteriorhodopsin (60 ng purple membrane) sample was prepared by drying a 1-μL droplet of a suspension of purple membrane fragments (50 μg/mL) onto the thinnest portion of the waveguide. The 3 strongest bands near 1650, 1550, and 1200 cm$^{-1}$ are due to amide I, amide II, and amide III vibrations, respectively, and are characteristic of the peptide backbone.

In comparison to prior art spectra of similar samples obtained using an IR microscope with planar waveguides 30–50 μm in thickness, the spectra of FIG. 10 have substantially improved signal-noise ratios for 10–20μ shorter measurement times. For example, the noise level in both of the spectra of FIG. 10 (obtained with 500 scans each) is 0.001 absorbance units, whereas in spectra obtained with the microscope-coupled planar waveguides, the noise level was typically 0.01 absorbance units for 10,000 or 20,000 scans.

At the same time, the absorbance signals are somewhat reduced (between 3- and 5-fold) for similar sized samples on the tapered 20-μm waveguide, as opposed to the untapered 30-μm waveguides with 45° bevels used previously in the prior art. The reduction in attenuation signals is due to the predominance in the tapered waveguide of light propagating at relatively low off-axis angles, i.e. angles that lie less than 45° away from the waveguide surface plane. Light in such modes is absorbed relatively inefficiently by molecules at the surface, giving rise to smaller attenuation signals per molecule.

The principal advantage of tapering thin Ge planar waveguides is to permit a substantial increase in throughput for a given sensor thickness, making it possible to detect the IR signal level more precisely in a shorter length of time. The increase in throughput results from filling the large numerical aperture of a high-index waveguide medium (Ge, n=4). With an untapered planar waveguide, the largest numerical aperture that can be attained inside the waveguide is equal to the numerical aperture of the element that focuses light through air onto the end of the waveguide.

On the other hand, the largest numerical aperture that can be propagated through a tapered waveguide is determined by the refractive index of the waveguide material and it's cladding, and is equal to $(n_1^2 - n_2^2)^{1/2}$ Here $n_1$ is the refractive index of the waveguide medium ($n_1$=4 for Ge), while $n^2$ is the highest refractive index of the cladding materials in contact with the waveguide ($n_2$=2.26 for ZnS). For the disclosed ZnS-clad Ge waveguide, this maximum numerical aperture is 3.3. Thus, ~4-fold more light energy can be propagated through the sensing region of a planar Ge waveguide than can be obtained by focusing light through air into the (untapered) waveguide edge.

Gradually tapering waveguide enables an increase in the numerical aperture. In such a taper, the product of the numerical aperture and waveguide thickness remains constant, as long as the maximum numerical aperture of the waveguide is not exceeded. A cone of light with numerical aperture of 0.3 that is transmitted into a 1-mm thick Ge waveguide maintains that numerical aperture across the air/Ge interface. Inside the Ge, it has a half-angular spread of only arcsine (0.3/4)=4°. It is possible to achieve a numerical aperture of 3.3 by gradually tapering the waveguide by a factor of about 10. That is, once a waveguide thickness of about 100 μm is reached, the numerical aperture of the waveguide is filled. At this thickness, the cone of propagating light rays extends all the way to the critical angle between Ge and ZnS, that is, to a half-angular spread of arcos (2.26/4)=56°.

The taper factor used herein (1 mm/20 μm=50) is much larger than the ratio of the maximum numerical aperture of the waveguide (3.3) to the numerical aperture of the input focusing optic (~0.3). This excess taper factor is intended to guarantee that, to the greatest extent possible, the numerical aperture of the sensing region of the waveguide is filled. With the particular light source present in the Midac spectrometer used herein, it is not difficult to fill the 1×1 mm input aperture of the tapered waveguide. Thus, a significant fraction of the input light is expected to be coupled out of the waveguide, i.e. to exceed the critical angle, as the waveguide is tapered down to its minimum thickness. It should be noted that the optimum apex to nadir ratio is dependent upon the detector size and shape and, when taken in conjunction with the teachings herein, will be apparent to those skilled in the art.

Much of the light that goes into one end of the waveguide is lost as it travels into the middle (thinnest) portion of the waveguide, but then as the light travels into the region where the waveguide tapers outward again, there is no further loss of light energy (or flux). The loss of light is therefore not due simply to the presence of non-parallel surfaces; but more specifically to the presence of surfaces that converge to a thickness less than ¼ of the input thickness. That is, nearly all the light present in the tapered region reaches the output face of the waveguide.

From here, the light is efficiently focused onto the 100-μm×100 μm area of the HgCdTe element in the Remspec detector. The use of an immersion lens in this detector provides an efficient coupling method that is extremely insensitive to the position of the fiber (or waveguide) output end. This greatly simplifies waveguide alignment, relative to the procedures that were required previously with a microscope. When incorporating a microscope, the output end of the waveguide had to be positioned at the very small focal area of the microscope's objective since the IR signal could be lost entirely with a mispositioning of as little as 50 μm.

The 1-mm width of the waveguide used in the example herein was chosen as the minimum width that could be easily manipulated without breaking. The thickness at the ends in these examples is the same as the width to match the square shape of the IR detector element used in the testing. The prism was then tapered as stated heretofore. Various taper ratios were tested with the result that the greater the thickness, the lower the sensitivity. A minimum 0.1-mm thickness, which corresponds to a taper ratio of 10, gave a high light throughput, but a lower (at least 5-fold) sensitivity to analyte at the surface than the 20 μm thickness. Test data (not shown) showed a continuous increase in sensitivity as the thickness of the waveguide decreased.

The wide range of propagation angles present at the sensing area of the tapered quasi-planar waveguide eliminates the distracting oscillatory transmission pattern that is observed for thin planar Ge waveguides. This is advantageous for a sensor, because it means that there are no sharp features in the spectrum that could be mistaken for absorption bands of a material present at the waveguide surface. Furthermore, the transmitted intensity at any frequency is not nearly as sensitive to waveguide alignment as with true planar waveguides.

The wide range of propagation angles present can lead to some degree of non-linearity of the absorbance signal, presenting small deviations from logarithmic response (i.e. the absorbance nonlinearities). In particular, the nonlinear response is not important for measurement of different spectra of samples that are subjected to an in situ perturbation while they are adsorbed or adhered to the surface of the waveguide. Additionally, the nonlinear response can be unimportant if there is a single known analyte, and a calibration curve can be established.

With the tapered waveguide, most of the internal reflections occur within a fairly small region near the point of minimum thickness. Thus, molecules located at the surface of this region predominate in the attenuation spectrum. This is a particular advantage for obtaining ATR spectra of small samples that must be kept submerged under water, e.g. biological samples. A relatively large pool of aqueous buffer can cover the surface of the entire waveguide and its supporting quartz substrate. Even when the entire waveguide is covered, this produces only about as much background attenuation as is shown in FIG. 10A, i.e. maximally 0.2–0.3 absorbance units. Meanwhile, a biological sample that covers only the ~1 mm$^2$ area above the thinnest portion of the waveguide can be detected and analyzed with great sensitivity.

The disclosed coupling method enables measurement of ATR-IR spectra using <100-μm thick planar waveguides in a horizontal configuration. The 20 μm thick waveguide affords high attenuation values for a small number of IR-absorbing molecules at the waveguide surface. This, and the improvement in signal/noise ratio obtained as a result of the coupling efficiency, make tapered Ge waveguides particularly well suited for measuring spectra of small biological samples, such as the detection of different spectra from various components of the cell membranes of individual frog eggs, 1.5 mm in diameter, that must be submerged under a bulk aqueous buffer.

Figure 11:
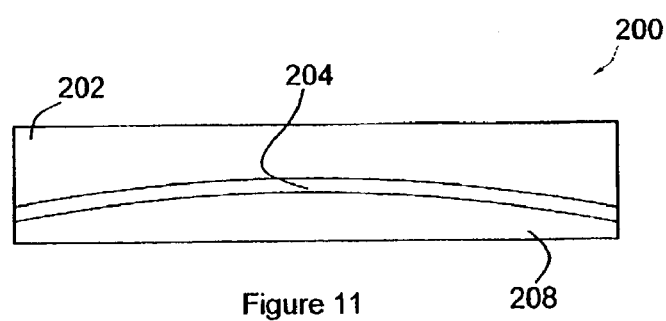
FIG. 11 is an alternate embodiment of the tapered waveguide

The quasi-tapered waveguide 200 illustrated in FIG. 11 is tapered as set forth above. The arcuate surface of the Ge prism 202 is then coated with a ZnS coating 204 and embedded into an epoxide substrate 208.

Figure 12:
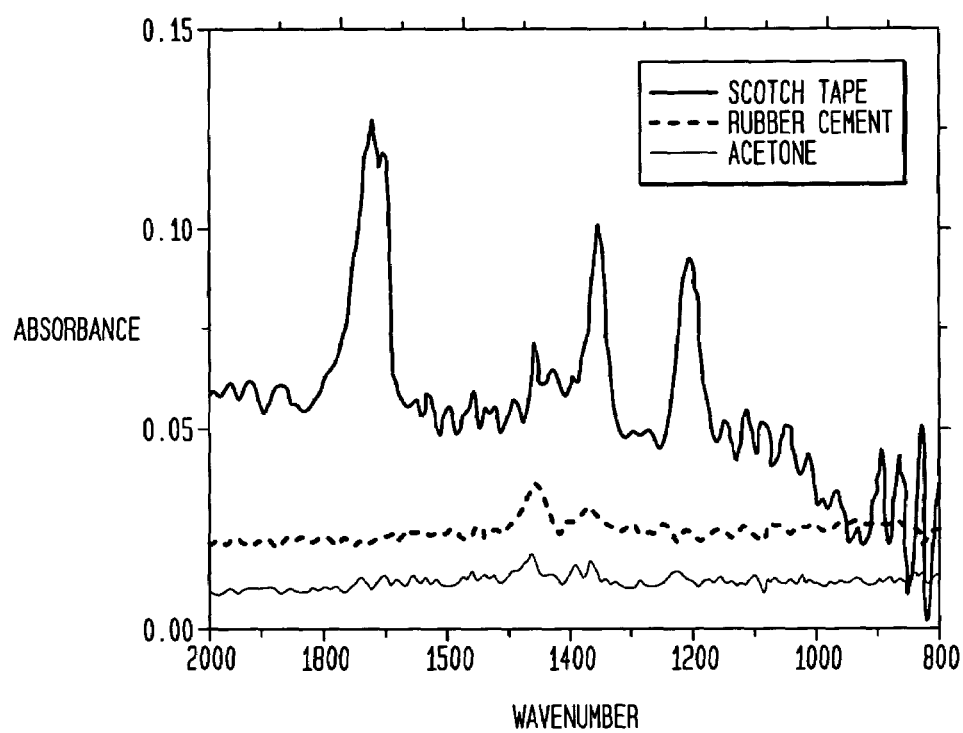
FIG. 12 is a graph illustrating the comparison spectra between acetone, rubber cement and Scotch® Tape using the waveguide of FIG. 11.

In FIG. 12 the graphed spectra illustrates the comparison between Scotch® Tape, rubber cement and acetone. The spectra were read using the waveguide 200 having a 12 μm waveguide nadir. As can be seen in the graph, the Scotch® Tape 300 and the rubber cement 302 have similar spectra, showing that the tape is invisible and that the only material readable is the adhesive. The acetone spectrum 304, however, provides a completely different spectrum reading than the two adhesives.

Figure 13:
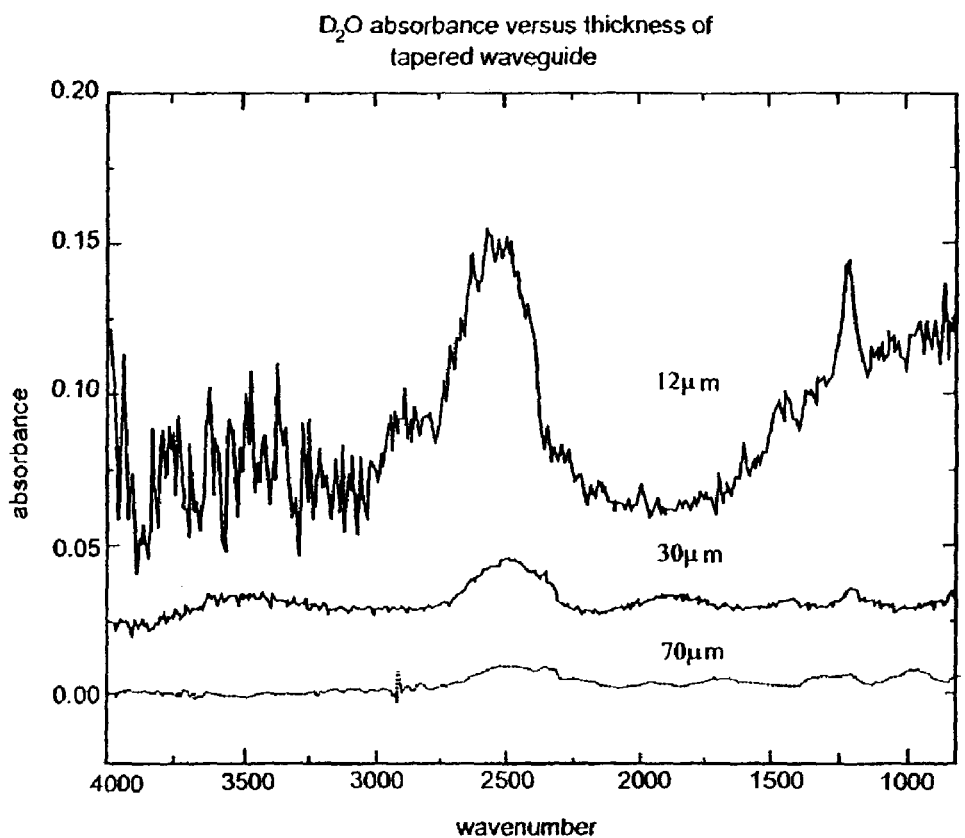
FIG. 13 illustrates the absorbance sensitivity of the waveguide of FIG. 11 for three thickness.
Figure 14:
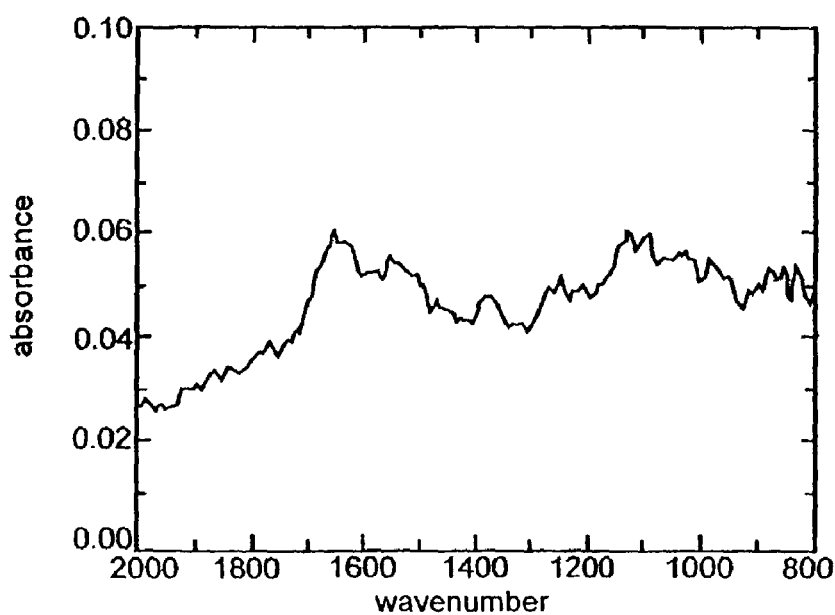
FIG. 14 is a graph of halorhodopsin using the waveguide of FIG. 11.

In FIG. 13 the absorbance spectrum of D2O, using the waveguide arrangement of FIG. 11, is compared at different waveguide thickness. As illustrated, the sensitivity of the waveguide increased dramatically when using a 12 μm waveguide. The overall sensitivity increase is substantially greater than the increase between the 70 μm and 30 μm readings. FIG. 14 illustrates the spectra of halorhodopsin using the 12 μm waveguide of FIG. 11.

The disclosed planar slab waveguides are the thinnest to date capable of evanescent-wave sensing in the mid-IR. When coupled to an IR microscope, these evanescent-wave sensors show a substantial improvement in surface sensitivity over thicker waveguides and fibers. These include gradually bi-tapering the waveguide by a factor of 4 or more in both its width and thickness. This will permit an even larger fraction of the guided light energy to be propagated as an evanescent wave at the waveguide's thinnest region, where is where the sensing of microscopic samples should take place. Tapering in this manner, rather than uniformly reducing the waveguide thickness, is a means of allowing more efficient coupling of light by the IR microscope into and out of all of the allowed modes of the thinnest region of the waveguide. A finer optical polish of the Ge surfaces will also enhance the detectivity by increasing the throughput.

Although the foregoing relates to measuring IR absorption spectra with broadband light, the waveguide design is also useful for making sensors based on monochromatic (e.g. laser) light. These sensors are useful for the study of very small samples, such as the membranes of single living cells.

What is claimed is:

1. A method of fabricating a quasi-planar waveguide, comprising the steps of:
   a- cementing a first surface of a polished IR transparent member to a substrate,
   b- grinding a second surface of said IR-transparent member to form an arcuate surface having apexes at opposing ends and a nadir in between,
   c- polishing said second surface to a predetermined thickness.

2. The method of claim 1 further comprising the step of polishing said second surface to have a thickness of less than 100 micrometers.

3. The method of claim 1 further comprising the step of polishing said arcuate surface to have a ratio of nadir to apex at opposing ends of up to about 0.25 to 1.

4. The method of claim 1 further comprising the step of polishing said arcuate surface to have a ratio of nadir to apex at opposing ends of up to about 0.02 to 1.

5. The method of claim 1, wherein said IR-transparent member is germanium.

6. The method of claim 1, further comprising the step of coating a surface of said IR-transparent member with a cladding, said cladding being a chemically vapor deposited layer of an IR-transparent material, said layer being from about 1 to about 5 microns in thickness and having a lower refractive index that of said IR-transparent member, said step of coating a surface of said IR-transparent member with a cladding, preceding said step of cementing said IR-transparent member to a substrate, said cladding being between said IR-transparent member and said substrate.

7. The method of claim 5, wherein said step of cladding comprises chemically vapor depositing a member selected from the group consisting of ZnS and ZnSe on said IR-transparent material.

8. The method of claim 1 further comprising the steps of:
   a. grinding said arcuate surface to proximate said nadir,
   b. minimizing light scattering by polishing said first surface to about a 0.1 µm finish,
   c. coupling directly to an IR detector,
   d. passing light from a light source, through said waveguide, to said IR detector,
      wherein said ratio between said apex and said nadir increases IR signal throughput.

9. A method of fabricating a quasi-planar waveguide, comprising the steps of:
   a- coating a first surface of an IR-transparent member with a cladding, said cladding being from about 1 to about 5 microns in thickness and having a lower refractive index that of said IR-transparent member,
   b- cementing said first surface of a polished IR transparent member to a substrate,
   c- grinding a second surface to a predetermined thickness to form an arcuate surface having apexes at opposing ends and a nadir in between
   e- polishing said second surface of said IR-transparent member to have a ratio of nadir to apex at said opposing ends of up to about 0.25 to 1, to about 0.02 to 1,
   f- coupling said waveguide to an IR detector;
   g- passing light from a light source, through said waveguide, to said IR detector.

10. The method of claim 9, wherein said IR-transparent member is germanium.

11. The method of claim 9 claim wherein said cladding is a chemically vapor deposited layer of an IR-transparent material.

12. The method of claim 9, wherein said step of cladding comprises chemically vapor depositing a member selected from the group consisting of ZnS and ZnSe on said IR-transparent material.

\* \* \* \* \*